United States Patent [19]
Balschmidt

[11] Patent Number: 5,840,680
[45] Date of Patent: *Nov. 24, 1998

[54] ASP^B28 INSULIN CRYSTALS

[75] Inventor: Per Balschmidt, Esperærde, Denmark

[73] Assignee: Novo Nordisk A/S, Bagsvaerd, Denmark

[*] Notice: The term of this patent shall not extend beyond the expiration date of Pat. No. 5,547,930.

[21] Appl. No.: 763,853

[22] Filed: Dec. 11, 1996

Related U.S. Application Data

[60] Continuation of Ser. No. 644,781, May 10, 1996, abandoned, which is a division of Ser. No. 127,672, Sep. 28, 1993, Pat. No. 5,547,930.

[30] Foreign Application Priority Data

Jun. 21, 1993 [DK] Denmark .................................. 727/93

[51] Int. Cl.$^6$ ............................. A61K 38/28; C07K 5/00; C07K 7/00; C07K 16/00
[52] U.S. Cl. .................................. 514/3; 514/4; 530/303; 530/304; 530/305
[58] Field of Search .......................... 514/3, 4; 520/303, 520/304, 305

[56] References Cited

U.S. PATENT DOCUMENTS

| | | | |
|---|---|---|---|
| 2,538,018 | 1/1951 | Krayenbühl et al. | 167/75 |
| 2,801,953 | 8/1957 | Dorzbach et al. | 167/75 |
| 2,849,370 | 8/1958 | Petersen et al. | 167/75 |
| 3,005,023 | 10/1961 | Miller | 260/559 |
| 3,019,173 | 1/1962 | Arishima et al. | 195/80 |
| 3,060,093 | 10/1962 | Poulsen et al. | 167/75 |
| 3,102,077 | 8/1963 | Christensen | 530/304 |
| 3,868,358 | 2/1975 | Jackson | 260/112.7 |
| 4,608,364 | 8/1986 | Grau | 514/4 |
| 5,028,587 | 7/1991 | Dorschug et al. | 514/3 |
| 5,149,777 | 9/1992 | Hansen et al. | 530/303 |
| 5,164,366 | 11/1992 | BalSchmidt et al. | 514/3 |
| 5,423,641 | 6/1995 | Jonassen et al. | 435/69.9 |
| 5,461,031 | 10/1995 | De Felippis | 514/4 |
| 5,474,978 | 12/1995 | Bakaysa et al. | 514/4 |
| 5,514,646 | 5/1996 | Chance et al. | 514/3 |
| 5,547,930 | 8/1996 | Balschmidt | 514/3 |

FOREIGN PATENT DOCUMENTS

| | | |
|---|---|---|
| 0214826 | 3/1987 | European Pat. Off. . |
| 0383472 | 8/1990 | European Pat. Off. . |
| 3327709 | 2/1985 | Germany . |
| 94151 | 3/1988 | Romania . |
| WO90/07522 | 7/1990 | WIPO . |
| WO95/00550 | 1/1995 | WIPO . |

OTHER PUBLICATIONS

Howey, et al., *Diabetes*, 43, 396–402 (Mar. 1994).
Brems, et al., *Protein Engineering*, 5:6, 519–525 (1992).
Heinemann, et al., *Diabetologia*, 33, 384–386 (1990).
Kirk–Othmer, *Encyclopedia of Chemical Technology* 13, 607–614 (1981).

Bruce H. Frank, Text and Slide copies given at the Conference on Insulin, Self Association and Conformational Studies on Human Proinsulin and Insulin Analogs, University of New York, Aug. 29–Sep. 1, 1989.
Fullerton, et al., *Biophys. Acta*, 214, 141–147 (1970).
*Diabetologia*, 30, 503A (1987).
Brange, et al., *Nature*, 333:16 679–682 (Jun. 1988).
Brange et al., *Diabetes Care*, 13:9, 923–954 (Sep. 1990).
Wollmer, et al., *Phenol–Promoted Structural Transformation of Insulin in Solution*, from the 2nd Assisi International Symposium on Advanced Models for the Therapy of Insulin–Dependent Diabetes 903–911 (Apr. 1986).
Brange, *Galenics of Insulin: The Physico–chemical and Pharmaceutical Aspects of Insulin and Insulin Preparations*, Springer–Verlag Berlin Heidelberg, Germany (1987).
Brems, et al, *Protein Engineering*, 5:6, 527–533 (1992).
Chen, et al., *Proc. Natl. Sci. Counc*, ROC(A), 6:3 185–189 (1982).
Galloway, et al., *Insulin Update*, 111–119 91982).
Balschmidt, et al., *Acta Cryst*, 975–986 (1991).
Dodson, et al., *Phil Trans. R. Soc. Lond. A* 345, 153–164 (1993).
Wollmer, et al., *Biol. Chem. Hoppe–Seyler*, 370, 1045–1053 (Sep. 1989).
Derewenda, et al., *Nature*, 338:13 594–596 (Apr. 1989).
Brader, et al., *Biochemistry*, 30, 6636–6645 (1991).
Harding, et al., *The Crystal Structure of Insulin: II. An Investigation of Rhombohedral Zinc Insulin Crystals and a Report of other Crystalline Forms*, Chemical Crystallography Laboratory, South Parks Road, Oxford, England, 212–226 (Nov. 8, 1965).
Brange, et al., *Structural Biology*, 1, 934–940 (1991).
Scott and Fisher, *J. Pharmacol. Exp. Ther.*, 58:78 (1936).
Hagedorn, et al., *J. Am. Med. Assn.*, 106:177–180 (1936).
Krayenbühl and Rosenberg, *Rep. Steno Mem. Hosp. Nord. Insulinlab.*, 1:60 (1946).
Goodman, *Fermentation and Mutation Development of the Tetracyclines*, Springer–Verlag Berlin Heidelberg, New York, Tokyo (1985).
Heinemann, *Action Profiles of Rapid–Acting Human Insulin Analogues*, Frontiers in Insulin Pharmacology International Symposium, Hamburg, pp. 87–96, Published by Georg Thieme Verlag Stuttgart–New York. Theime Medical Publishers, Inc.–New York (1993).
Brange, et al., *Acta Pharm Nord*, 4(3):149–158 (1992).
Brems, et al., Altering the Self–Association and Stability of Insulin by Amino Acid Replacement, Protein Folding: In Vivo and In Vitro, American Chemical Society, Chaptr. 19, (1993).

(List continued on next page.)

Primary Examiner—Cecilia J. Tsang
Assistant Examiner—Jennifer Harle
Attorney, Agent, or Firm—Steve T. Zelson, Esq.; Valeta A. Gregg, Esq.

[57] ABSTRACT

The present invention relates to insulin crystals comprising ASP^B28 and protamine, and pharmaceutical preparations containing same. The crystals and preparations exhibit rapid onset and prolonged activity when administered in vivo.

14 Claims, 3 Drawing Sheets

OTHER PUBLICATIONS

Oral Presentations of the 28th Annual Meeting of the European Association for the Study of Diabetes, Prague, Czechoslavakia (Sep. 8–11, 1992).

*J. British Diabetic Association*, Posters, p. S33.

Directions in Diabetes Research III, A Lilly Symposium Held in Indianapolis, Indiana, Jun. 10–11, 1993.

Brange, et al., "Design of Novel Insulins with Changed Self–Association and Ligand Binding Properties" *GBF Monographs*, 12:140–144 (1988).

(Invited Speaker) Self–Association and Conformational Studies on Human Proinsulin and Insulin Analogs, B.H. Frank Lilly Research Laboratories, Eli Lilly & Co., Indiana, IN 46285.

Wiefels, et al., "Insulin kinetics and Dynamics in Insulin—dependent Diabetic Patients after Injections of Human Insulin or the Insulin Analogues X14 and X14+Zn", pp. 97–101. *Diabetologia*, 36 [Supp. 1]: A1–A222, 29th Annual Meeting of the European Association for the Study of Diabetes, Abstract, Istanbul, Turkey, Sep. 6–10, 1993.

Lutterman, et al., *Glycaemic Control in IDDM Patients during One Day with Injection of Human Insulin or the Insulin Analogues Insulin X14 and Insulin X14 (+Zn)*, Frontiers in Insulin Pharmacology International Symposium, Hamburg, pp. 102–109, Published by Georg Thieme Verlag Stuttgart–New York, Theime Medical Publishers, Inc.–New York (1993).

Kim, et al.,*Biochem. and Biophys. Res. Comm.*, 186(2):1115–1120 (1992).

Smith, et al., *Biopolymers*, 32:441–445 (1992).

Smith, et al., *Proteins: Structure, Function, and Genetics*, 14:401–408 (1992).

Derewenda, et al., *British Medical Bulletin*, 45 (1):4–18 (1989).

Brange, *Current Opinion in Structural Biology*, 1:934–940 (1991).

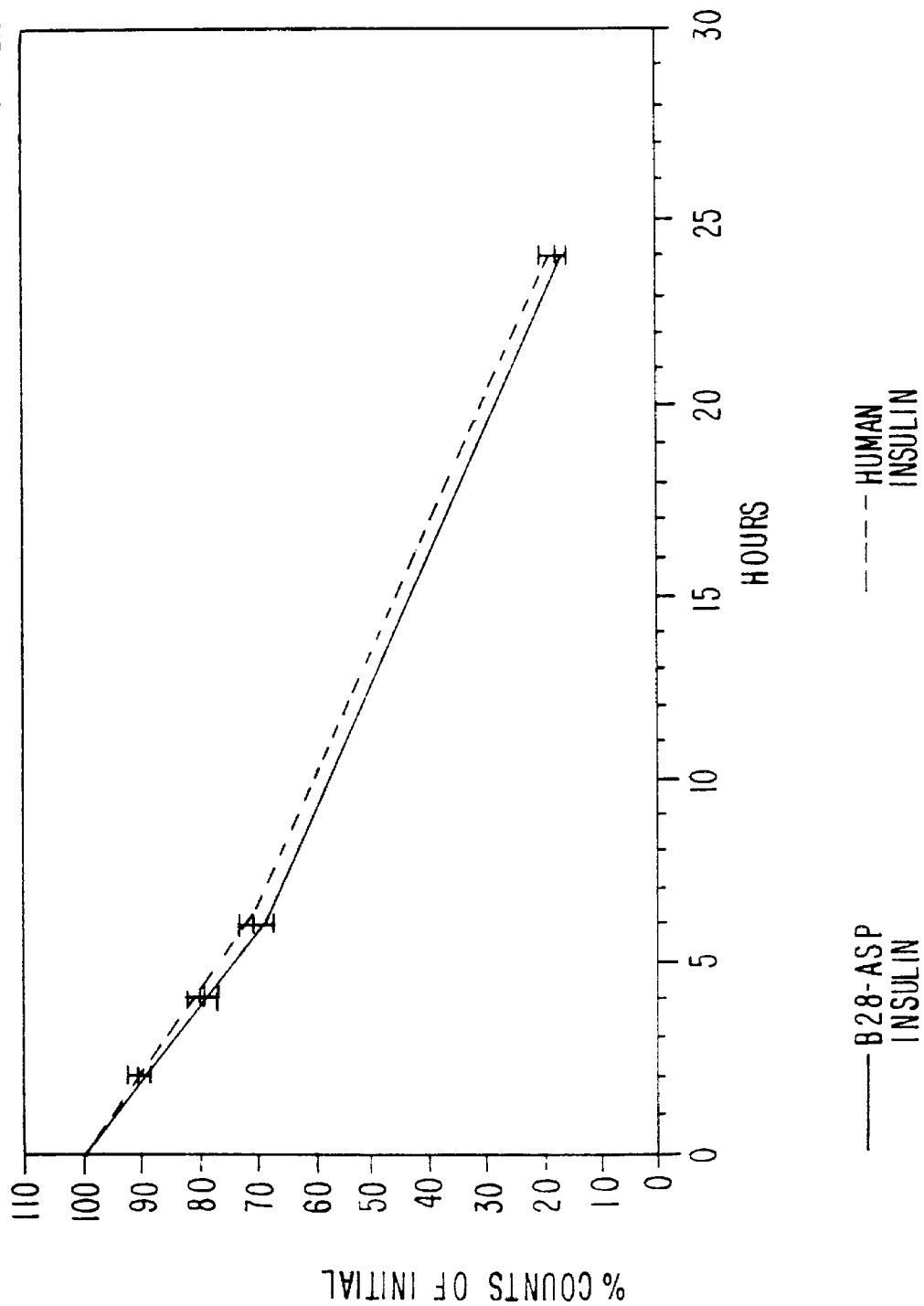

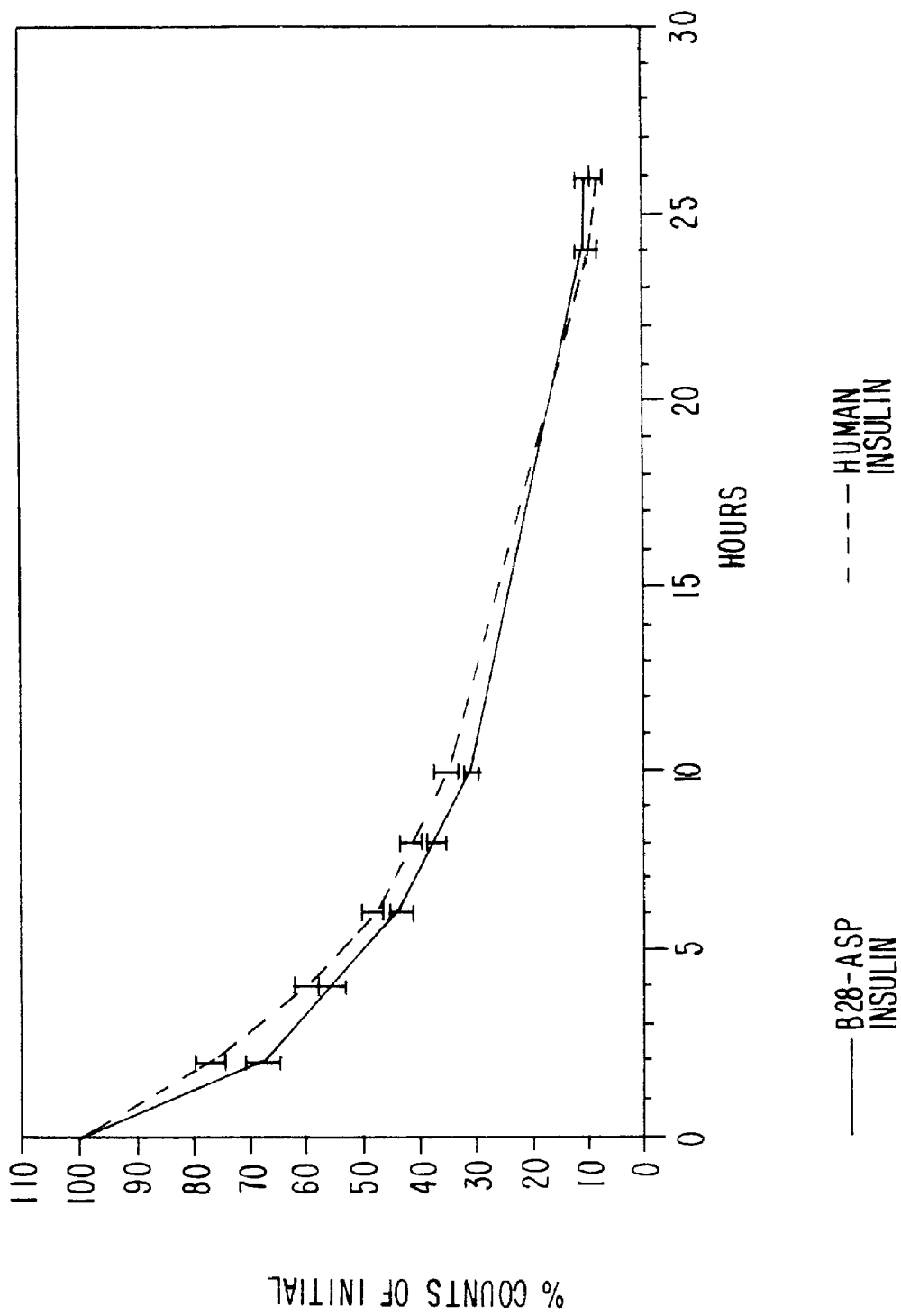

ASP$^{B28}$ INSULIN CRYSTALS

This is a continuation of application Ser. No. 08/644,781, filed May 10, 1996 now abandoned which is a division of U.S. Ser. No. 08/127,672, filed Sep. 28, 1993, now U.S. Pat. No. 5,547,930.

The present invention relates to crystals of Asp$^{B28}$ human insulin and to preparations containing such crystals.

THE TECHNICAL FIELD

Diabetes is a general term for disorders in man having excessive urine excretion as in diabetes mellitus and diabetes insipidus. Diabetes mellitus is a metabolic disorder in which the ability to utilize glucose is more or less completely lost. About 2% of all people suffer from diabetes. If a diabetic patient is not treated properly, diabetes mellitus results in hyperglycemia giving symptoms like thirst, hunger, emaciation and weakness. Diabetes also gives rise to imperfect metabolism of fats with resulting acidosis, sometimes leading to dyspnoea, lipidemia, ketonuria and, finally, coma. Diabetes mellitus is frequently associated with progressive weakening of the small vessels, particularly by affecting the eye and kidney, and atherosclerosis, and there may also be lowered resistance to pyrogenic infections. Patients having no or too low production of insulin can be treated with insulin preparations.

In the treatment of diabetes mellitus, many varieties of insulin preparations have been suggested and used. As diabetic patients are treated with insulin for several decades, there is a major need for safe and life quality improving insulin preparations. Some of the commercial available insulin preparations are characterized by a fast onset of action and other preparations have a relatively slow onset but show a more or less prolonged action. Fast acting insulin preparations are usually solutions of insulin, while retarded acting insulin preparations can be suspensions containing insulin in crystalline and/or amorphous form precipitated by addition of zinc salts alone or by addition of protamine or by a combination of both. In addition, some patients are using preparations having both a fast onset of action and a more prolonged action. Such a preparation may be an insulin solution wherein protamine insulin crystals are suspended. Some patients do themselves prepare the final preparation by mixing an insulin solution with a suspension preparation in the ratio desired by the patient in question.

Normally, insulin preparations are administered by subcutaneous injection. What is important for the patient, is the action profile of the insulin preparation which is the action of insulin on the glucose metabolism as a function of the time from the injection. In this profile, inter alia, the time for the onset, the maximum value and the total duration of action are important. A variety of insulin preparations with different action profiles are desired and requested by the patients. One patient may, on the same day, use insulin preparations with very different action profiles. The action profile requested is, for example, depending on the time of the day and the amount and composition of any meal eaten by the patient.

BACKGROUND ART

The first stable neutral insulin suspension was developed by Scott and Fischer (*J. Pharmacol. Exp. Ther.* 58 (1936), 78) who discovered that the presence of a surplus of protamine and a zinc salt (2 $\mu$g zinc per IU (international Unit) insulin) could stabilize the protamine insulin preparation, described by Hagedorn et al.: *J. Am. Med. Assn.* 106 (1936), 177–180.

Protamine Zinc Insulin made according to the United States or European Pharmacopoeias contains amorphous protamine zinc insulin as well as crystalline Protamine Zinc Insulin. Freshly prepared protamine zinc insulin contains mainly amorphous precipitate which will partly be transformed into crystalline particles upon storage, leading to a more protracted effect.

A completely crystalline protamine zinc insulin modification designated NPH insulin or Isophane Insulin was developed by Krayenbühl and Rosenberg (see *Rep. Steno Mem. Hosp. Nord. Insulinlab.* 1 (1946), 60; and Danish patent No. 64,708). They found that insulin and protamine brought together in isophane proportions at a neutral pH value in the presence of a small amount of zinc and phenol, or a phenol derivative, preferably m-cresol, will form an amorphous precipitate which upon standing is gradually but completely transformed into oblong tetragonal crystals limited at the ends by pyramidal faces. Insulin and salmon protamine co-crystallize in a weight ratio corresponding to about 0.09 mg protamine sulphate per mg insulin. Zinc in an amount of at least 3.5 $\mu$g per mg insulin and a phenol in a concentration higher than 0.1% is necessary for the preparation of the tetragonal crystals.

In the early days, this kind of crystals were prepared using porcine and bovine insulin from natural sources, but from the eighties, also human insulin, made by genetic engineering or by semisynthesis, is used.

Human insulin consists of two polypeptide chains, the so-called A and B chains which contain 21 and 30 amino acids, respectively. The A and B chains are interconnected by two cystine disulphide bridges. Insulin from most other species has a similar constitution, but may not contain the same amino acids at corresponding positions in the chains as in human insulin.

The development of the process known as genetic engineering has made it possible easily to prepare a great variety of insulin compounds being analogous to human insulin. In these insulin analogues, one or more of the amino acids have been substituted with other amino acids which can be coded for by the nucleotide sequences. As human insulin, as explained above, contains 51 amino acid residues, it is obvious that a large number of insulin analogues is possible and, in fact, a great variety of analogues with interesting properties have been prepared. In human insulin solutions with a concentration of interest for injection preparations, the insulin molecule is present in associated form as a hexamer (Brange et al. *Diabetes Care* 13, (1990), 923–954). After subcutaneous injection, it is believed that the rate of absorption by the blood stream is dependent of the size of the molecule, and it has been found that insulin analogues with amino acid substitutions which counteract or inhibit this hexamer formation have an unusual fast onset of action (Brange et al.: Ibid). This is of great therapeutic value for the diabetic patient.

In the crystals of the prolonged acting protamine insulin preparations, the insulin is also found to be hexameric (Balschmidt et al.: *Acta Chryst.* B47, (1991), 975–986) and as far as we are aware, no examples on crystallization of genetic engineered or (semi)-synthetic prepared low associating insulin analogues with protamine have been published hitherto.

One object of this invention is to prepare protamine containing crystals of a low associating insulin analogue which conveniently can be used for insulin preparations.

Another object of this invention is to prepare protamine containing insulin analogue crystals which enables mixed preparations having both a very rapid onset of insulin action and a prolonged insulin action.

BRIEF STATEMENT OF THIS INVENTION

Surprisingly, it has been found that when combining the insulin analog AspB28 human insulin which is almost monomeric in solution (Brange et al.: Ibid) with protamine in the presence of small amounts of zinc and a phenol, it is possible to prepare NPH insulin like crystals which fulfil the physical requirements for suspension preparations, i.e. slowly sedimentation and easy resuspension. In contrast, for example, it has not been possible to prepare a suitable suspension of crystals of another very similar insulin analogue, the $Glu^{B28}$ human insulin which structurally only differs from the $Asp^{B28}$ analogue by an additional methylene group in the amino acid side chain.

BRIEF DESCRIPTION OF THE DRAWINGS

FIG. 2 is a graph of the rate of disappearance of NPH human insulin and of $ASP^{B28}$ human insulin from the injection site following subcutaneous injection.

FIG. 3 is a graph of the rate of disappearance of human insulin Mixtard preparation and of $Asp^{B28}$ human insulin from the injection site following subcutaneous injection.

DETAILED DESCRIPTION OF THIS INVENTION

Figure 1A:
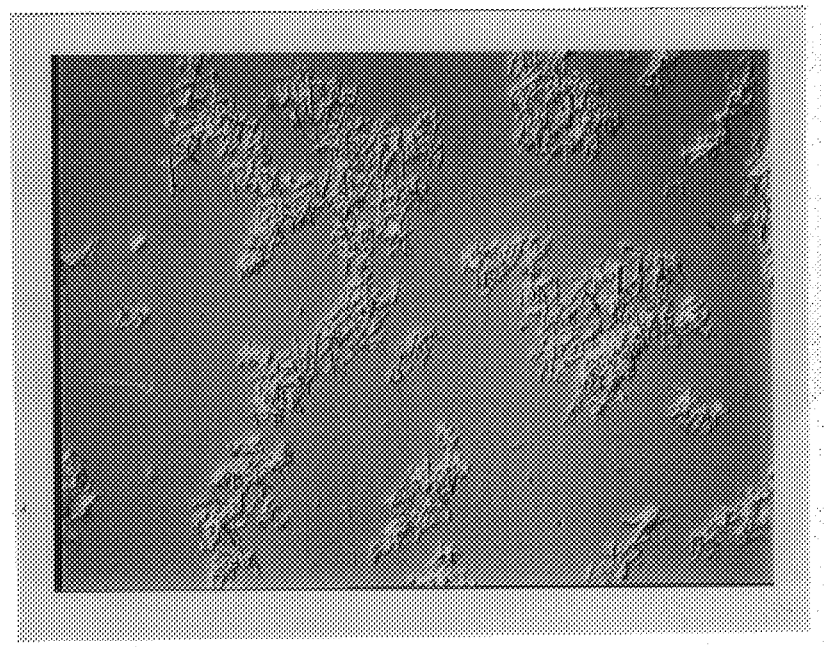
FIG. 1a is a photomicrograph of $Asp^{B28}$ human insulin NPH crystals.

One aspect of this invention is crystals comprising $Asp^{B28}$ human insulin and protamine. If desired, said crystals also contain zinc. Another aspect of this invention is pharmaceutical preparations comprising crystals comprising $Asp^{B28}$ human insulin, protamine and, if desired, zinc. Said preparations are preferably in an aqueous medium.

Protamine is the generic name of a group of strongly basic proteins present in sperm cell nucleic in saltlike combination with nucleic acids. Commercially available protamines can be isolated from mature fish sperm and are usually obtained as the sulphate. The peptide composition of a specific protamine may vary depending of which family, genera or species of fish it is obtained from. Normally, protamines to be used together with insulin are obtained from salmon (salmine) or rainbow trout (iridine). Protamine from salmon or trout can be separated into two or three main fractions of proteins which may be separated further. The different parent peptides consist of about 30 amino acids of which more than 20 are arginines. The average molecular weight of protamine is about 4,300. Preferably, protamine sulphate of high purity is used.

In a preferred embodiment of this invention, the content of protamine in the crystals of this invention is in the range from about 10 to about 15% (weight/weight) of protamine, preferably from about 12.5 to about 14% (weight/weight) of protamine.

The content of zinc in the crystals and preparations of this invention may wholly or partially originate from a zinc salt such as zinc chloride, zinc sulphate or zinc acetate which is added during the manufacturing of the preparations.

In a preferred embodiment of this invention, the content of zinc in the crystals of this invention is in the range from about 0.35 to about 1.5% (weight/weight) zinc, preferably from about 0.5 to about 1% (weight/weight) zinc. In another preferred embodiment of this invention, the total content of zinc (in bound and, optionally, in free form) in the preparation of this invention is in the range from about 0.3 µg through about 2 µg zinc per IU of $Asp^{B28}$ human insulin.

In a further, preferred embodiment of this invention, the total content of $Asp^{B28}$ human insulin (in crystalline and optionally in dissolved form) in the preparations of this invention is in the range from about 10 through about 500 IU/ml, preferably in the range from about 20 through about 200 IU/ml, most preferred in the range from about 40 through about 100 IU/ml.

In a further, preferred embodiment of this invention, the preparations of this invention have a pH value in the range from about 6.5 through about 8, preferably in the range from about 7 through about 7.5, most preferred in the range from about 7.2 through about 7.4.

In a still further, preferred embodiment of this invention, the crystals and preparations of this invention contain phenol or a derivative thereof such as m-cresol acetic acid ester. In said crystals, the phenol or phenol derivative is believed to be build into the crystal lattice. Probably, said crystals contain one molecule of phenol per molecule of $Asp^{B28}$ human insulin resulting in crystals containing about 1.5% (weight/weight) of phenol.

A preferred embodiment of this invention is preparations of this invention wherein the content of phenol or a derivative thereof is in the range from about 0.05 through about 2% (weight/volume), preferably in the range from about 0.1 through about 0.6% (weight/volume).

The crystals and the preparations of this invention can be prepared similarly to the crystals and preparations described by Krayenbühl and Rosenberg (ibid).

The process of crystallizing $Asp^{B28}$ human insulin together with protamine was rather slow and lasted for about a week. However, the resulting crystals showed the usual NPH crystal appearance and size. As a consequence of the additional carboxyl group in the $Asp^{B28}$ human insulin molecule, the isophane ratio was found substantially higher than with conventional mammalian insulins, but the high protamine content was not reflected in the subcutaneous disappearance test in pigs, as the disappearance curves of the $^{125}$I-labelled $Asp^{B28}$ human insulin NPH crystals and human insulin NPH crystals were found virtually overlapping.

Thus, $Asp^{B28}$ human insulin formulated as a NPH preparation is a new useful intermediately acting insulin preparation, especially when used in combination with dissolved $Asp^{B28}$ human insulin.

A very desired insulin preparation should exhibit both a very fast onset and a prolonged action. Such a preparation could be formulated as a mixture of a dissolved monomeric insulin analogue and a suspension of human insulin NPH crystals. Unfortunately, such a preparation has turned up not to be stable, as an exchange between the human insulin in the crystals and the dissolved insulin analogue slowly takes place and thus impairs the very fast acting properties of the preparation.

A preparation containing exclusively $Asp^{B28}$ human insulin both in the dissolved phase and in the NPH crystals are stable and have shown to exhibit a very rapid onset of absorption as well as a prolonged absorption by the subcutaneous disappearance test of a $^{125}$I-labelled preparation in pigs.

Such a preparation can be produced in a manner known per se, for example, by mixing a suspension of $Asp^{B28}$ human insulin NPH crystals with a solution of $Asp^{B28}$ human insulin. The ratio of such mixtures may be from about 10% to about 50%, preferably about 30% insulin analogue solution and from about 50% to about 90%, preferably about 70% insulin analogue crystals suspension. Consequently, a preferred embodiment of this invention is a preparation of this invention containing both dissolved Asp$^{B28}$ human insulin and crystals comprising Asp$^{B28}$ human insulin. A still further preferred embodiment of this invention is preparations of this invention wherein the ratio between crystals comprising Asp$^{B28}$ human insulin and protamine, on one hand, and dissolved Asp$^{B28}$ human insulin, on the other hand, is in the range from about 90:10 to about 50:50, preferably about 70:30.

The preparations of this invention can be prepared by mixing the different constituents such as Asp$^{B28}$ human insulin, protamine, optionally a zinc salt, for example zinc chloride, a preservative, for example phenol, an isotonic agent, for example sodium chloride or glycerol, and a buffer, for example disodium monohydrogen phosphate, in an aqueous medium. One way of doing this is to prepare an acidic solution of Asp$^{B28}$ human insulin, protamine sulphate, zinc chloride, phenol and glycerol, for example by use of diluted hydrochloric acid. This solution is then slowly mixed with a sodium phosphate solution with stirring at room temperature, and after mixing, the pH value of the mixture is, if desired, adjusted to a pH value of about 7.3.

The preparations of this invention are used for diabetic therapy, preferably to human beings, similarly to the usual commercial preparations, for example, as prescribed by the physician.

Any novel feature or combination of features described herein is considered essential to this invention.

This invention is further illustrated by the following examples which, however, are not to be construed as limiting.

EXAMPLE 1

Asp$^{B28}$ human insulin NPH preparation

A crystal suspension was prepared from the following two solutions:

Solution I: 197.5 mg Asp$^{B28}$ human insulin, 400 μl 1 n hydrochloric acid, 359 μl Zn$^{++}$ solution (5 mg/ml), 2.57 ml protamine sulphate solution (10 mg/ml), 12.5 ml 0.3% m-cresol, 0.13% phenol, 3.2% glycerol and water ad 25 ml.

Solution II: 5.0 ml 0.13M disodium monohydrogenphosphate, 12.5 ml 0.3% m-cresol, 0.13% phenol, 3.2% glycerol and water ad 25 ml.

Solution II was added to solution I and the pH value was readjusted to 7.30. The resulting suspension was left at 20° C. for 24 hours followed by standing for 6 days at 4° C. for complete crystallization.

Disappearance test

The protracted action was evaluated by the disappearance of $^{125}$I-labelled Asp$^{B28}$ human insulin NPH in comparison to $^{125}$I-labelled human insulin NPH after subcutaneous injection in pigs. The insulin analogue preparation was formulated as shown above with the exception that an amount of $^{125}$I-labelled Asp$^{B28}$ human insulin/human insulin, corresponding to an activity of 2 μCi/ml in the final preparation, has been added before the crystallization. The test was set up with 6 pigs, each receiving 100 μl test preparation (Asp$^{B28}$ human insulin) on one side of the neck and 100 μl standard preparation (human insulin) on the other side. The remaining radioactivity at the injection sites was measured at suitable intervals by external γ-counting.

Results

Figure 1B:
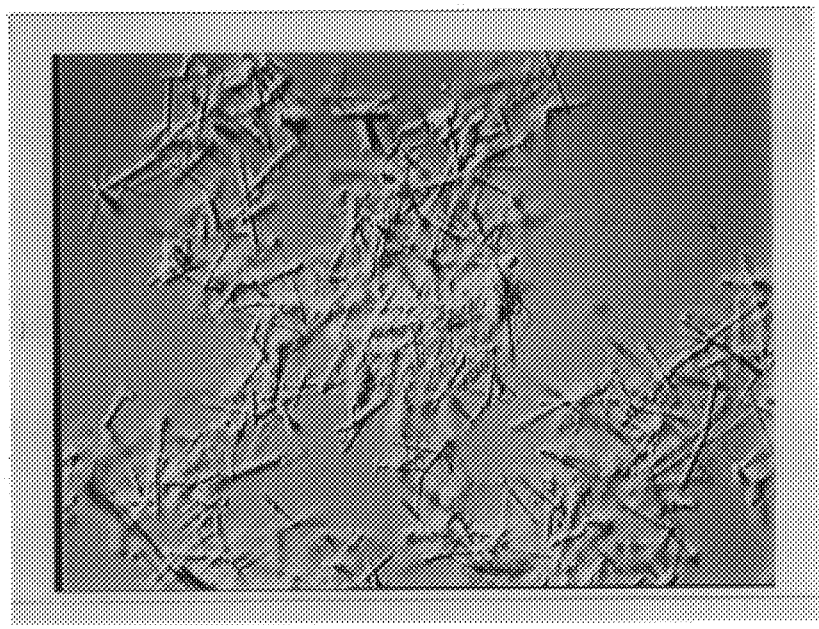
FIG. 1b is a second photomicrograph of $Asp^{B28}$ human insulin NPH crystals.

The Asp$^{B28}$ human insulin NPH crystals showed the same thin rod-shaped image as in the human insulin NPH preparation and had a length of 6–8 μm. The microscopic appearance of the preparation is shown at two different magnifications on the photographs in FIG. 1.

The subcutaneous disappearance test of the $^{125}$I-labelled Asp$^{B28}$ human insulin NPH preparation showed that the rate of disappearance from the injection site was very similar to the disappearance of the labelled human insulin NPH preparation. The $T_{50\%}$ value (i.e. the time for 50% remaining radioactivity) was found to be 10.1±1.0 hours versus 10.9±0.9 hours for the standard NPH preparation (human insulin). The results are illustrated in graphic form in FIG. 2.

Conclusions

Asp$^{B28}$ human insulin has been found able to crystallize with protamine by the usual NPH preparation procedure, but standing for a week was necessary for complete crystallization. The resulting crystal suspension had the usual appearance known from the human insulin NPH preparation.

Evaluated by a subcutaneous disappearance test in pigs, the action profile of the Asp$^{B28}$ human insulin NPH preparation was not found different from a human insulin NPH preparation.

EXAMPLE 2

Mixed dissolved and NPH preparation of Asp$^{B28}$ human insulin

A crystal suspension was prepared from the following two solutions:

Solution I: 158.1 mg Asp$^{B28}$ human insulin, 130 μl 1N hydrochloric acid, 142 μl Zn$^{++}$ solution (10 mg/ml), 2.087 ml protamine sulphate solution (10 mg/ml), 2.0 ml 3% phenol, 16% glycerol and water ad 25 ml.

Solution II: 4.0 ml 0.13M disodium monohydrogen phosphate, 2.0 ml 3% phenol, 16% glycerol and water ad 25 ml.

Solution II was added to solution I and the pH value was readjusted to 7.30. The resulting suspension was left at 20° C. for 24 hours followed by standing for 6 days at 4° C. for complete crystallization.

A solution was prepared by dissolving 39.5 mg Asp$^{B28}$ human insulin in 2 ml water by addition of 32 μl 1M hydrochloric acid and then 7.4 μl Zn$^{++}$ solution (10 mg/ml), 1.0 ml 3% phenol, 16% glycerol, 1.0 ml 0.13M disodium monohydrogen phosphate and finally water ad 10 ml was added. The resulting pH value was 7.27.

The final mixed preparation was prepared by addition of 6 ml of the solution to 14 ml crystal suspension, thus forming a 30/70 ratio of fast acting and prolonged acting insulin analogue.

After standing over night at 20° C. the relative amount of dissolved protein in the supernatant was determined by reversed phase HPLC.

Disappearance test

The action profile was evaluated by the disappearance of $^{125}$I-labelled Asp$^{B28}$ human insulin mixed preparation in comparison to a $^{125}$I-labelled human insulin Mixtard® 30/70 preparation after subcutaneous injection in pigs. Mixtard® is a trademark for insulin preparations containing both dissolved human insulin and suspended insulin. Mixtard® 30/70 contains 30% dissolved insulin and 70% suspended insulin. The insulin analogue preparation was formulated as shown above, with the exception that an amount of $^{125}$I-labelled analogue, corresponding to an activity of 1.7 μCi/ml in the final preparation, has been added together with the cold analogue. The test was set up as described in example 1.

Results

The mixed Asp$^{B28}$ human insulin preparation showed a similar relative amount of dissolved protein in the supernatant as in a human insulin Mixtard® 30/70 preparation when analyzed by reversed phase HPLC.

The subcutaneous disappearance test of the mixed Asp$^{B28}$ human insulin preparation showed that the rate of disappearance from the injection site was substantially faster during the first hours than for the human insulin Mixtard® preparation, but later the rates became very similar. The $T_{75\%}$ value (i.e. the time for 75% remaining radioactivity) was found to be 1.6±0.5 hours versus 2.2±0.5 hours for the human insulin Mixtard® standard. The $T_{50\%}$ values were found to 4.9±1.0 hours versus 5.7±1.0 hours and the $T_{75\%}$ values to 12.8±2.3 hours versus 13.4±2.4 hours, respectively. The results are illustrated in graphic form in FIG. 3.

Conclusions

It has been possible to formulate a mixed preparation of dissolved and NPH crystallized Asp$^{B28}$ human insulin which by a subcutaneous disappearance test in pigs have shown a substantially faster initial and a similar prolonged absorption profile as found for a standard human insulin Mixtard® 30/70 preparation.

I claim:

1. Crystals comprising Asp$^{B28}$ human insulin, protamine, and a member selected from the group consisting of phenol, a m-cresol, or a combination thereof.

2. Crystals as defined in claim 1, further comprising zinc.

3. A pharmaceutical formulation comprising crystals as defined in claim 1.

4. A pharmaceutical formulation comprising crystals as defined in claim 2.

5. A pharmaceutical formulation as defined in claim 3, wherein said crystals are suspended in an aqueous medium.

6. A pharmaceutical formulation as defined in claim 4, wherein said crystals are suspended in an aqueous medium.

7. A pharmaceutical formulation as defined in claim 3, further comprising a member selected from the group consisting of an isotonic agent, a buffer, and a combination thereof.

8. A pharmaceutical formulation as defined in claim 4, further comprising a member selected from the group consisting of an isotonic agent, a buffer, and a combination thereof.

9. A pharmaceutical formulation as defined in claim 7, wherein said isotonic agent is selected from the group consisting of sodium chloride and glycerol and said buffer comprises disodium monohydrogen phosphate.

10. A pharmaceutical formulation as defined in claim 8, wherein said isotonic agent is selected from the group consisting of sodium chloride and glycerol and said buffer comprises disodium monohydrogen phosphate.

11. A pharmaceutical formulation as defined in claim 3, further comprising dissolved Asp$^{B28}$ human insulin.

12. A pharmaceutical formulation as defied in claim 4, further comprising dissolved Asp$^{B28}$ human insulin.

13. A method of treating a patient suffering from diabetes mellitus, said method comprising administering to said patient a pharmaceutical composition as defined in claim 3.

14. A method of treating a patient suffering from diabetes mellitus, said method comprising administering to said patient a pharmaceutical composition as defined in claim 4.

* * * * *

UNITED STATES PATENT AND TRADEMARK OFFICE
CERTIFICATE OF CORRECTION

PATENT NO. : 5,840,680
DATED : November 24, 1998
INVENTOR(S) : Per Balschmidt

It is certified that error appears in the above-identified patent and that said Letters Patent is hereby corrected as shown below:

In the claims:

Column 7, line 27: delete "a" before m-cresol

Column 8, line 23: delete "defied", insert --defined--

Signed and Sealed this

Tenth Day of October, 2000

Attest:

Q. TODD DICKINSON

*Attesting Officer*          *Director of Patents and Trademarks*